(12) United States Patent
Allred et al.

(10) Patent No.: US 7,740,479 B2
(45) Date of Patent: Jun. 22, 2010

(54) ACTIVATING BRUSH TIP APPLICATORS FOR DENTAL BLEACHING COMPOSITIONS

(75) Inventors: Peter M. Allred, Riverton, UT (US); David Q. Vu, West Jordan, UT (US)

(73) Assignee: Ultradent Products, Inc., South Jordan, UT (US)

( * ) Notice: Subject to any disclaimer, the term of this patent is extended or adjusted under 35 U.S.C. 154(b) by 143 days.

(21) Appl. No.: 11/866,532

(22) Filed: Oct. 3, 2007

(65) Prior Publication Data

US 2009/0092563 A1    Apr. 9, 2009

(51) Int. Cl.
*A61C 5/04* (2006.01)
(52) U.S. Cl. .......................................... 433/90; 433/89
(58) Field of Classification Search .................. 433/80, 433/89, 90; 604/19, 39, 39.01, 161, 239–243, 604/272–275; 424/50, 53
See application file for complete search history.

(56) References Cited

U.S. PATENT DOCUMENTS

| | | | |
|---|---|---|---|
| 5,301,381 A | 4/1994 | Klupt | |
| 5,611,687 A | 3/1997 | Wagner | |
| 6,108,850 A | 8/2000 | McLaughlin | |
| 6,485,709 B2 * | 11/2002 | Banerjee et al. | 424/53 |
| 6,547,467 B2 * | 4/2003 | Quintero | 401/132 |
| 6,599,126 B1 | 7/2003 | Sale et al. | |
| 6,648,641 B1 | 11/2003 | Viltro et al. | |
| 6,726,482 B2 | 4/2004 | Atkins et al. | |
| 6,908,607 B2 | 6/2005 | Banerjee et al. | |
| 6,988,892 B2 | 1/2006 | Dragon et al. | |
| 7,201,577 B2 | 4/2007 | Levine | |
| 7,264,026 B2 | 9/2007 | Gruber et al. | |
| 2002/0155071 A1 | 10/2002 | McLaughlin | |
| 2003/0194678 A1 | 10/2003 | Viltro et al. | |
| 2005/0175956 A1 | 8/2005 | Russell et al. | |
| 2005/0233279 A1 | 10/2005 | Zeh et al. | |
| 2007/0015112 A1 | 1/2007 | Hochman et al. | |
| 2009/0074679 A1* | 3/2009 | Silverman | 424/53 |

* cited by examiner

*Primary Examiner*—Cris L Rodriguez
*Assistant Examiner*—Eric Rosen
(74) *Attorney, Agent, or Firm*—Workman Nydegger

(57) ABSTRACT

A brush tipped applicator includes an applicator tip having a body defining an external surface and an internal conduit. The applicator tip body can have a proximal end defining a proximal opening of the internal conduit and a distal end. The proximal end of the applicator tip body can have a first fastener that is configured for being coupled to a fastener (i.e., second fastener) of a member containing the dental bleaching composition such that the internal conduit of the applicator tip body is capable of being fluidly coupled with the dental bleaching composition. Additionally, the brush tip includes at least one filament disposed on the external surface of the applicator tip body. A dental bleach activator disposed within the filament in an amount sufficient for activating the dental bleaching composition for whitening the teeth.

20 Claims, 3 Drawing Sheets

ACTIVATING BRUSH TIP APPLICATORS FOR DENTAL BLEACHING COMPOSITIONS

BACKGROUND OF THE INVENTION

1. The Field of the Invention

The present invention relates to a dental bleach applicator that includes a brush tip configured to activate a dental bleach. More particularly, the present invention relates to a dental bleach applicator that contains a substantially inactive or partially activated dental bleach composition, and that includes a brush tip having brush filaments impregnated with an activator that can activate the dental bleach.

2. The Relevant Technology

Teeth generally become more darkly pigmented with age and exposure to materials such as tea, coffee and the like. It has long been a goal of dentistry to provide a means to safely and effectively reverse this darkening process and increase the whiteness of teeth. Historically, there are two approaches to the problem. The first involves removing pigmentation that has adhered onto the surface of the teeth. This is commonly achieved through the use of abrasives, which can be augmented with solvents. While rapidly effective, these techniques have the disadvantage of only being able to remove extrinsic stains, leaving all internal pigmentation unchanged. Thus, the whitening effect is extremely limited.

A more recent innovation involves a method of using oxidizing agents to penetrate into the tooth structure and bleach out the undesired pigmentation. Typical tooth bleaching agents release active oxygen radicals. Such bleaching agents include peroxides, such as hydrogen peroxide, percarbonates and perborates of the alkali and alkaline earth metals, or complex compounds containing hydrogen peroxide. It is also known that peroxide salts of the alkali or alkaline earth metals and peroxyacetic acid are useful in whitening teeth.

Commonly used dental bleaching agents include carbamide peroxide, also called urea hydrogen peroxide, hydrogen peroxide carbamide, and perhydrol-urea. Carbamide peroxide has been used by dental clinicians for several decades as an oral antiseptic. Tooth bleaching was an observed side effect of extended contact time. Over-the-counter compositions of 10% carbamide peroxide are available as GLY-OX-IDE® by Marion Laboratories and PROXIGEL® by Reed and Carnrick. A sticky bleaching gel, able to hold a comfortable-fitting dental tray in position for an extended time period, is available under the trademark OPALESCENCE® from Ultradent Products, Inc. in South Jordan, Utah.

In-office bleaching compositions can be presently categorized as being either a one-part or two-part system. The distinction is based upon whether all of the components of the bleaching composition are self-contained in a desired pre-mixed proportion or if the active ingredients are isolated and need to be mixed and proportioned before use. In the two-part system the components which would otherwise interact with the peroxide bleaching agent are physically separated from one another. The one-part system may be more attractive based upon convenience of application in contrast to the two-part system, which requires both mixing and proportioning the isolated components prior to use. Another problem with the two part systems of prior art is that the concentration of the peroxide is reduced by 50% when a 1:1 ratio is mixed together. However, in reality, the distinction between a one-part and two-part system has no significance clinically or upon the end result. Accordingly, what should be of concern is the ability to independently control the activity of the peroxide bleaching agent to minimize the need for repeated applications and/or office visits, while at the same time achieving extended shelf life.

In view of the foregoing, there is an ongoing need for improved bleaching compositions, systems, and methods that are simple and easy to use. Such improvements would be expected to improve or encourage compliance by the user. Therefore, it would be advantageous to have a dental bleach applicator that incorporates the benefits of a one-part system and a two-part system. Additionally, it would be beneficial to have a dental bleach applicator that includes a single bleaching composition and an activator separated from the bleaching composition, such that the activator can be admixed into the bleaching composition during use.

BRIEF SUMMARY OF THE INVENTION

Generally, the present invention provides an improved dental bleach applicator that is simple and easy to use, and that is designed to reduce the likelihood of the bleaching composition coming into unfavorable contact with the gums, buccal tissue, tongue, lips, or other part of the oral cavity. Also, the present invention provides a dental bleach applicator that incorporates the benefits of a one-part system and a two-part system. Additionally, the present invention provides a dental bleach applicator that includes a bleaching composition and an activator separated from the bleaching composition, such that the activator can be admixed into the bleaching composition for activation during use. Furthermore, the present invention provides a dental bleach applicator that contains a dental bleach composition that can be activated, and a brush tip having brush filaments impregnated with an activator that can activate the dental bleach.

In one embodiment, the present invention includes a brush tip for applying a dental bleaching composition to teeth. The brush tip includes an applicator tip having a body defining an external surface and an internal conduit. The applicator tip body has a proximal end defining a proximal opening of the internal conduit, and a distal end that is associated with a conduit opening. The proximal end of the applicator tip body has a first fastener that is configured for being, coupled to a fastener (i.e., second fastener) of a member containing the dental bleaching composition, such that the internal conduit of the applicator tip body is capable of being fluidly coupled with the dental bleaching composition. Additionally, the brush tip includes at least one filament that can be contained on the external surface of the applicator tip body. A dental bleach activator is disposed within the filament in an amount sufficient for activating the dental bleaching composition for whitening the teeth.

In one embodiment, the present invention is a brush tipped applicator for applying a dental bleaching composition to teeth. The brush tipped applicator includes an applicator body having a reservoir of a dental bleaching composition and a dispenser mechanism configured for dispensing the dental bleaching composition. A brush tip is coupled to the applicator body. Such a brush tip includes an applicator tip body defining an external surface and an internal conduit. The applicator tip body has a proximal end defining a proximal opening of the internal conduit, and a distal end defining a distal opening (e.g., conduit opening) of the internal conduit. Alternatively, the conduit can have an external opening somewhere other than the distal end, for example, on the external surface or laterally from the conduit. The proximal end of the applicator tip body is coupled to the applicator body such that the internal conduit of the applicator tip is fluidly coupled with the dental bleaching composition. The brush tip includes at least one filament disposed on the external surface of the applicator tip body. A dental bleach activator is disposed within the filament in an amount sufficient for activating the dental bleaching composition for whitening the teeth.

In one embodiment, at least one filament of the brush tip includes an amount of activator sufficient for multiple applications of the dental bleaching composition to teeth. This includes the amount of activator being sufficient for activating an amount of the dental bleaching composition sufficient for at least 2 separate applications of the dental bleaching composition to the teeth.

In one embodiment, the filament is comprised of a polymer impregnated with dental bleach activator. This includes a polymer that is configured so as to control the release of the dental bleach activator into the dental bleaching composition. For example, the polymer can be comprised of polyvinylpyrrolidone or nylon. Also, the filament can be a bristle, flocked member, porous body, foam, or the like.

In one embodiment, the filament is disposed adjacent to a bleaching composition dispensing conduit opening of the internal conduit. Usually, the conduit opening is located at the distal end of the brush tip body. However, the conduit opening can be located at any point along the tip body.

In one embodiment, the filament or plurality of filaments form a contact area when in contact with a tooth, where the contact area is less than the surface area of a front surface of a tooth. In one example, the contact area is less than about 1 $cm^2$.

In one embodiment, the proximal end of the applicator tip has a first fastener removably coupled to a fastener (e.g., second fastener) of the applicator body.

In one embodiment, the applicator body is a syringe.

In one embodiment, dental bleach applicator is not a tooth brush and/or the brush tip is not a toothbrush head.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
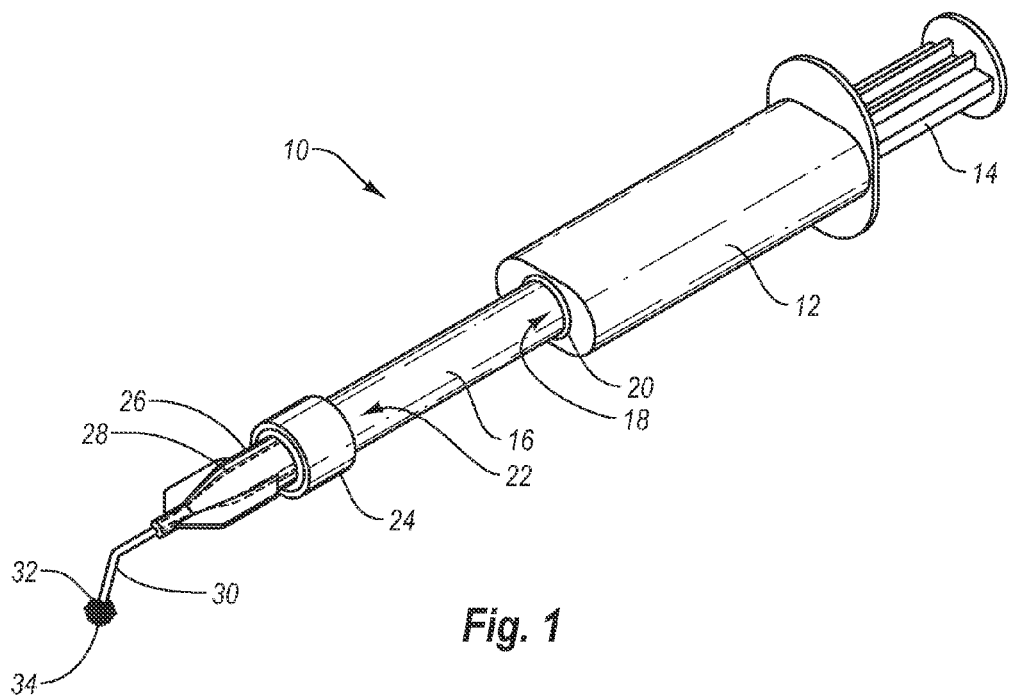
FIG. 1 is a schematic representation of an embodiment of a dental bleach applicator having a brush tip.

Generally, the present invention provides a dental bleach applicator that retains a dental bleaching composition and a brush tip that includes an activator for activating the dental bleaching composition impregnated within the brush filaments. The activator is used to activate a dental bleaching composition into an active or more active form for use in whitening teeth. During use, the dental bleach applicator applies the dental bleach and activator to teeth in a manner that causes a reaction such that a significant portion of the bleaching compound is activated so as to have sufficient bleaching function within in a short period of time.

The applicator has any form of a device that can dispense the dental bleach composition. Examples of applicators include syringes, pumps, dispensers, and the like, which include a reservoir containing a bleaching composition, and a means for dispensing the bleaching composition. The brush tip has any form that includes at least one brush filament disposed thereon in a manner that allows the brush filaments to apply, spread, coat, and/or paint the dental bleach composition onto teeth so that the activator impregnated within the brush filaments diffuses into the dental bleach composition so as to activate the bleaching agent.

I. Introduction

In one embodiment, the invention provides a dental bleach applicator comprising a dental bleaching composition that is capable of being activated for use in whitening teeth. The dental bleaching composition can be configured as substantially inactive, partially activated, less than optimally active, or having normal bleaching activity so long as the activator enhances the bleaching composition activity. The applicator is used in conjunction with an applicator tip that includes at least one filament made from a material, such as a polymer, that allows for a dental bleach activator disposed within the filament to diffuse therethrough and/or out from the filament. The filament is a flexible or resilient polymeric composition, such as a plastic or elastomer that is fabricated into an applicator filament. The applicator tip and/or filament is dimensioned such that an effective amount of the bleaching compound can be dispensed therefrom, and such that an effective amount of the dental bleach activator can diffuse into and activate the dental bleaching composition. Additionally, the applicator and/or applicator tip is configured such that the activator induces and/or furthers the activation of a significant portion of the bleaching compound within minutes.

In one embodiment, the invention provides a brush tip for use with a dental bleach applicator. Such a brush tip includes at least one brush filament or a plurality of brush filaments. The brush filaments are configured similar to the bristles of a paintbrush, painting device, hairbrush, toothbrush, or the like. At least one of the filaments contains a dental bleach activator. Alternatively, a single, larger filament is disposed on the brush tip, and can have various shapes and sizes.

In one embodiment, the invention provides a method for using a dental bleach applicator with a brush tip in order to whiten teeth. Such a method includes the following: providing a dental bleach applicator containing a dental bleaching composition; providing a brush tip having at least one brush filament impregnated with a dental bleach activator; dispensing the dental bleaching composition from the brush tip;

contacting the brush filament impregnated with the dental bleaching composition such that the activator activates the dental bleaching composition; and spreading the activated dental bleaching composition on the teeth. Alternatively, the dental bleaching composition is spread onto the teeth with the brush filament as the activator is diffusing into and activating the dental bleaching composition. In another alternative, the dental bleaching composition can be dispensed from the brush tip directly onto the teeth or directly onto the brush filament impregnated with the activator.

II. Dental Bleach Applicator

The present invention includes dental bleach applicators that may have various shapes, sizes, configurations, and functionalities. That is, the dental bleach applicators are not limited to any particular configuration, but usually include an applicator body having a dispenser mechanism and an applicator tip (e.g., brush tip). The applicator body and/or dispenser mechanism can be configured similar to syringes, pumps, toothpaste tubes, pressurized containers, pressurized dispensers, squirt bottles, lotion pumps, squeeze bottles, one-way valves, and the like.

In one embodiment, the dispenser mechanism is configured to be manually activated so as to cause an amount of the dental bleaching composition to be dispensed from the applicator. For example, the dispenser mechanism is configured to manually dispense the dental bleaching composition similar to a syringe, pump, or the like. Alternatively, the dispenser mechanism activates a mechanism that allows for a pressurized dental bleaching composition to be dispensed from the applicator, which can be exemplified by a typical pressurized shaving cream dispenser mechanism. While various applicator and dispenser mechanism configurations have been described, the present invention can include other configurations that allow for a dental bleaching composition to be retained and selectively dispensed for use.

In one embodiment, the dispenser mechanism is configured for dispensing a metered amount of the dental bleaching composition. That is, the dispenser mechanism is actuated so as to cause a specific amount of the dental bleaching composition to be dispensed. For example, the amount of dispensed dental bleaching composition per dispenser mechanism actuation is sufficient to cover a portion of a tooth, a whole tooth, a portion of a dental arch, a whole dental arch, and even the entire dentition. The amount of dispensed dental bleaching composition can be metered by a single dispenser mechanism actuation, or by visual markers that identify the amount of dental bleaching composition retained within the applicator and/or dispensed therefrom (e.g., syringe markings). In some instances, the dispenser mechanism is configured to dispense an amount that is predetermined by manufacturing selections or by user selections. The dispenser mechanism can have a single predetermined amount or a selection of predetermined amounts that can be selected prior to use.

In one embodiment, the dispenser mechanism is configured or set to dispense a determined amount of dental bleaching composition. For example, the dispenser mechanism is configured or set to dispense the dental bleaching composition in an amount per dispenser mechanism actuation ranging from about 0.1 ul to about 1 ml, more preferably from about 1 ul to about 500 ul, and most preferably from about 10 ul to about 100 ul.

The applicator tip can be configured into various shapes, sizes, configurations, and functionalities in order to provide the activator to the dental bleaching composition. The applicator tip includes a body that defines a conduit and a conduit opening (e.g., bleaching composition dispensing conduit opening) that is configured for dispensing or applying the dental bleaching composition. The conduit and conduit opening is any appropriate shape and size. The applicator tip is configured to be integrated with an applicator body or be removably coupled with an applicator body. In the instance of being configured to be attached to and removed from the applicator body, the applicator tip includes a fastening means at a proximal end of the applicator tip body that is associated with a corresponding fastening means on the distal end of the applicator body. Examples of the fastening means include leur fittings, threaded couplings, snap couplings, tongue-and-groove couplings, adhesive, and the like.

In one embodiment, the applicator tip is a brush tip. As such, the body of the brush tip has at least one brush filament associated therewith. While different embodiments of the brush filament are disposed in a variety of arrangements and orientations, it is beneficial for the brush filaments to be disposed in an arrangement and orientation that allows the brush tip to be used for applying the dental bleaching composition to the teeth. For example, the brush filaments are disposed adjacent to the conduit opening, around the conduit opening, covering the conduit opening, opposite of the conduit opening, along the tip body, circumferentially around the tip body, on one portion of the tip body, on one side of the tip body, or the like.

The brush filaments can also be configured into various shapes, sizes, configurations, and functionalities in order to provide the activator to the dental bleaching composition. This includes filaments that are conical, rectangular, cubic, cylindrical, wedge-like, spherical, oblong, symmetrical, asymmetrical, or the like. However, it is preferable for the brush tip and/or brush filaments to be a small size that allows for the dental bleaching composition to be applied to a single tooth, or even small enough to apply the dental bleaching composition to a portion of the tooth. It is especially preferable for the size of the brush tip and/or brush filaments to be small enough to allow for the dental bleaching composition to be selectively applied to a portion of a tooth without contacting the gums or having excessive contact with the gums. A brush tip and/or brush filaments that have a contact area with the tooth that is smaller than the size of a tooth surface allows for the dental bleaching composition to be selectively applied without the brush tip and/or brush filaments inadvertently contacting the gums. Similarly, it is preferable that the brush tip and/or brush filaments have a shape and size that allows for selective placement of the dental bleaching composition without contacting the tongue, buccal tissue, and/or lips. As a comparison, a standard toothbrush has a head and bristles that provide a contact area that is larger than the front surface of a tooth and use of such a tooth brush usually results in substantial contact between the toothbrush head and/or bristles with the gums, tongue, buccal tissue, and/or lips. However, toothpaste is typically not as caustic in comparison to a dental bleaching composition, which allows for the toothbrush head and/or bristles to have a larger contact surface area without detriment to the user. On the other hand, a brush tip and/or brush filaments that provide a contact area that is substantially smaller than the front surface of a tooth can reduce the incidences of accidental contact between the dental bleaching composition with the gums, tongue, buccal tissue, and/or lips. For example, the brush tip is a microbrush.

In one embodiment, dabbing the brush filaments onto a tooth forms a contact area that is about the size of the front surface (e.g., buccal side) of a tooth, more preferably less than the size of the front surface of a tooth, even more preferably less than about 0.75% of the front surface of a tooth, still more preferably less than about 0.5% of the front surface of a tooth, and most preferably less than about 0.25% of the front surface of a tooth.

In one embodiment, the contact area of the brush filaments is less than about 1 cm$^2$, more preferably less than about 0.75 cm$^2$, even more preferably less than about 0.5 cm$^2$, still more preferably less than about 0.25 cm$^2$, and most preferably less than about 0.15 cm$^2$.

In one embodiment, the brush filament or plurality of brush filaments include at least one dental bleach activator. As such, the brush filaments are prepared from a material that retain the activator therein when the applicator is not in use, and also allow the activator to diffuse therefrom when the filament comes into contact with the dental bleaching composition. The activator can be homogeneously or heterogeneously distributed throughout the filament. Also, the activator can be retained within reservoirs or depots within the filament. As such, any disposition of activator within the filament that allows a sufficient amount to activate the dental bleaching composition can be utilized.

FIG. 1 is a schematic representation of dental bleach applicator in the form of a dental bleach syringe 10. The dental bleach syringe 10 includes a barrel 12 and plunger 14. As is common with syringes, the barrel 12 is configured to retain a composition, such as the dental bleaching composition, and the plunger 14 is configured to dispense the composition from the barrel 12. Additionally, the dental bleach syringe 10 can include any component of any type of syringe. Accordingly, the dental bleach syringe 10 can be modified to include any features of syringes that are well known in the art.

As illustrated, the dental bleach syringe 10 includes an optional applicator tube 16 that is used to dispense the composition (e.g., dental bleaching composition) from the barrel 12. That is, the applicator tube 16 extends from the barrel 12 at a length sufficient to allow the dental bleach syringe 10 to administer the composition in the mouth with the barrel 12 and plunger 14 being sufficiently distanced from the mouth to allow manual manipulation of plunger 14. The applicator tube 16 includes a proximal end 18 that is configured to be coupled to the barrel 12 through a tube-barrel proximal coupling 20. Additionally, the applicator tube 16 includes a distal end 22 that is configured to be coupled to an applicator tip 26 through a tube-tip distal coupling 24. The tube-barrel proximal coupling 20 and/or the tube-tip distal coupling 24 can be any type of permanent or removable coupling, such as those commonly employed with syringes. In instances the applicator tube 16 is not utilized, the dental bleach syringe is directly coupled to the tip 26 via a coupling. Alternatively, the tip 26 includes the applicator tube 16.

The distal end of the dental bleach syringe 10 includes an applicator tip 26 at the distal end 22 of the tube 16 and fastened thereto by the coupling 24. The tip 26 includes a conduit 28 (shown by dashed lines) that is configured for dispensing or applying the composition onto teeth. The tip 26 is curved as shown, or it can be substantially straight or other configuration. The tip 26 includes a dental bleach applicator brush 30 that is configured for brushing or otherwise applying the composition onto the teeth after being dispensed from the conduit 28. The applicator brush 30 includes applicator brush filaments 32 in association with the conduit 28 such that the composition dispensed from the conduit 28 can come into contact with the applicator brush filaments 32. The applicator brush filaments 32 are impregnated with an activator 34 that activates the dental bleach composition from an inactive form to an activated form that can perform a dental bleaching function. Accordingly, the activator 34 is disposed in the applicator brush filaments 32 such that the activator 34 diffuses from the filaments 32 into the composition that is dispensed from the conduit 28.

Figure 2:
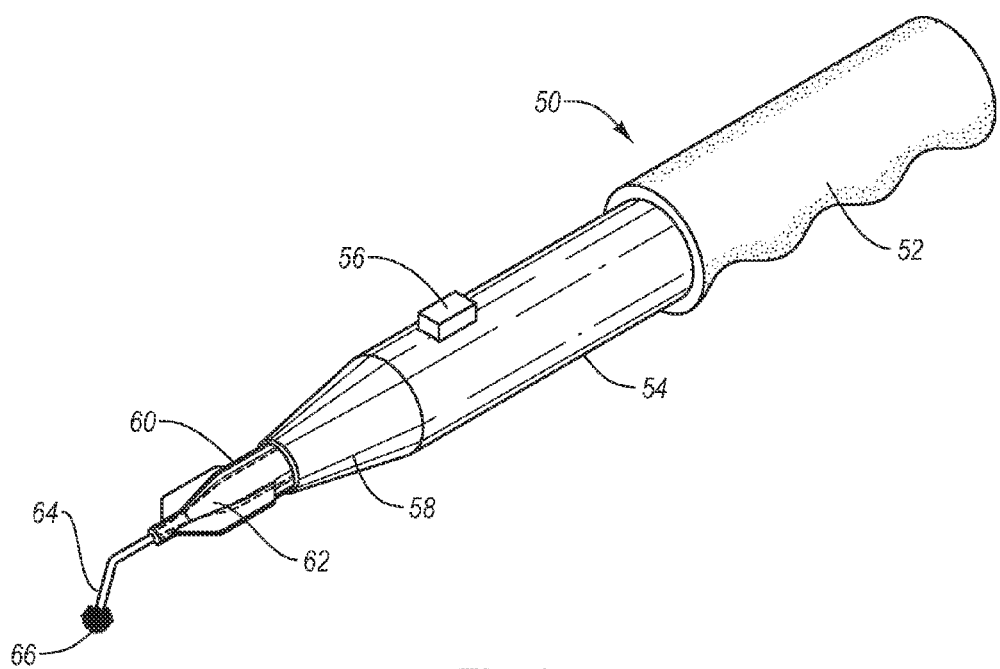
FIG. 2 is a schematic representation of an embodiment of a dental bleach applicator having a brush tip.

FIG. 2 is a schematic representation of another embodiment of a dental bleach applicator in the form of a dental bleach pump 50. The dental bleach pump 50 includes a handle 52 that optionally includes an ergonomic shape, as shown. The handle is configured for retaining a composition, such as a dental bleach composition. The pump 50 includes a barrel 54 that has a trigger 56 associated therewith. The trigger 56 is manipulated to cause the composition to be dispensed from the pump 50. The trigger 56 can be formed into a variety of shapes, sizes, and configurations in order to dispense the composition from the pump 50. Additionally, the barrel 54 is coupled to an optional extender 58 that is in turn coupled to an applicator tip 60. The applicator tip 60 includes a conduit 62 that passes the composition to the applicator brush 64 so that the composition can come into contact with activator-impregnated brush filaments 66.

Figure 3:
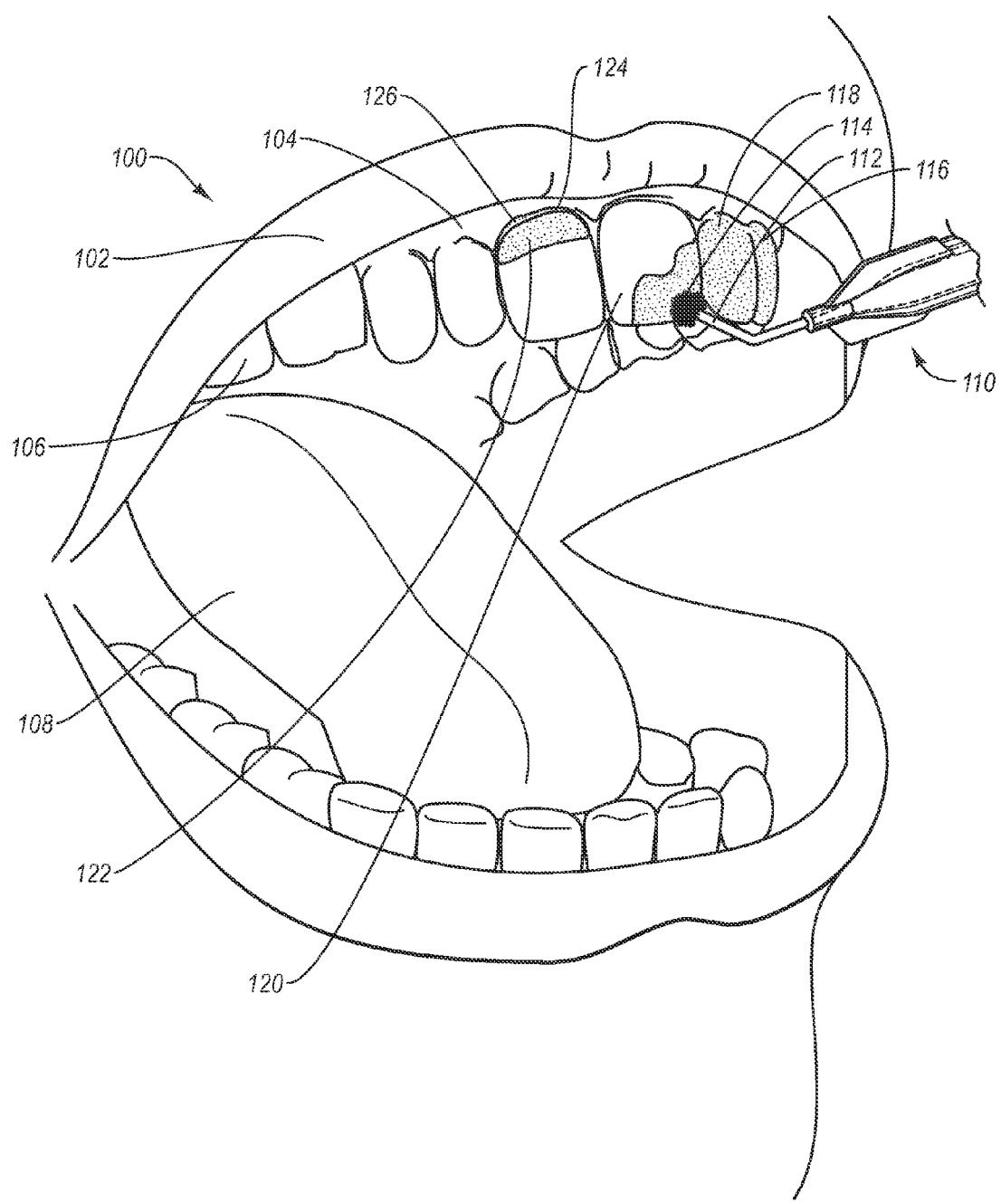
FIG. 3 is a schematic representation of an embodiment of a dental bleach activator having a brush tip that is selectively applying an activated dental bleaching composition to teeth.

FIG. 3 is a schematic representation of a mouth 100 that includes lips 102, gums 104, teeth 106, and a tongue 108, all of which may come into contact with a dental bleaching composition when the composition is applied to teeth 106. However, the lips 102, gums 104, and tongue 108 are sensitive to an activated dental bleaching composition such that contact therewith can cause chemical burns and severe discomfort. Additionally, FIG. 3 shows a dental bleach applicator 110 having an applicator brush 112, and brush filament 114 that is in the process of applying an activated dental bleaching composition 116 to the teeth 106. The dental bleaching composition 116 is activated by absorbing the activator from the brush filament 114.

The applicator brush 112 and/or the brush filaments 114 are sized and shaped so as to enable the dental bleach applicator 110 to selectively apply the activated bleaching composition 116 to selected portions of a single tooth 118. As shown, a tooth 118 is substantially coated with the activated bleaching composition 116 by being spread thereon with the applicator brush 112. Alternatively, a tooth 120 may be only partially coated with the activated bleaching composition 116 such that portions of the tooth 120 are devoid of having the activated bleaching composition disposed thereon. Accordingly, the applicator brush 112 and/or the brush filaments 114 provide a contact area with the tooth that is substantially smaller in comparison with a tooth, front surface of such a tooth, and/or contact area provided by a toothbrush.

The small size of the applicator brush 112 and/or brush filaments 114 (e.g., contact area) enables the activated dental bleaching composition 116 to be selectively applied to the teeth 106 without contacting the lips 102, gums 104, and/or tongue 108. However, the closer the applicator brush 112 and/or brush filaments 114 are maneuvered relative to the lips 102, gums 104, and/or tongue 108, the more chance that some of the activated dental bleaching composition 116 can come into contact therewith. As shown as an example in FIG. 3, the activated dental bleaching composition 116 is applied to a tooth 122 with a major portion 124 being applied to the tooth 122 with a minor portion 126 being applied to the gums 104. Thus, the small shape and size of the applicator 112 and/or brush filaments 114 allow for enhanced selectivity in applying the activated dental bleaching composition 116 to the teeth 106 without a substantial amount that causes a chemical burn to contact the lips 102, gums 104, and/or tongue 108.

Figures 4A, 4B:
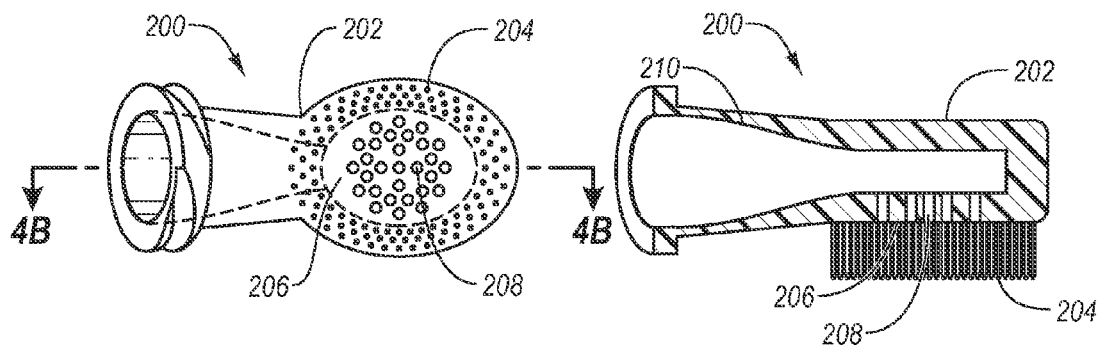
FIGS. 4A-4B are schematic representations of a bottom view and cutaway side view, respectively, of an embodiment of a brush tip applicator.

FIG. 4A is a schematic representation of an embodiment of a brush tip 200. The brush tip 200 has a shape generally defined by the brush head 202, which is substantially the shape as shown or any other possible shape in accordance with the present invention. The brush head 202 defines a composition conduit 210 that opens to at least one conduit opening 208 (e.g., dental bleaching composition conduit dispenser opening). The brush head 202 includes a plurality of brush filaments 204 disposed around the edge of the brush face 206; however, the filaments 204 can be disposed in any possible pattern and/or orientation. The brush face 206 is also shown to include a plurality of conduit openings 208. The conduit openings 208 can also be disposed in any possible pattern and/or orientation. In some instances, the brush face 206 includes only a single conduit opening 208.

FIG. 4B is a schematic representation of a cutaway view of a cross-section of the brush tip 200 of Figure A. The brush tip 200 is depicted with the brush head 202 including a composition conduit 210 that is fluidly coupled with the conduit opening 208 on the brush face 206. Accordingly, the dental bleaching composition can be delivered through the conduit 210 and dispensed out of the conduit openings 208 so as to contact the brush filaments 204 that are impregnated with the dental bleach activator so that the activator can diffuse into the composition and activate the bleach.

Figures 5A, 5B:
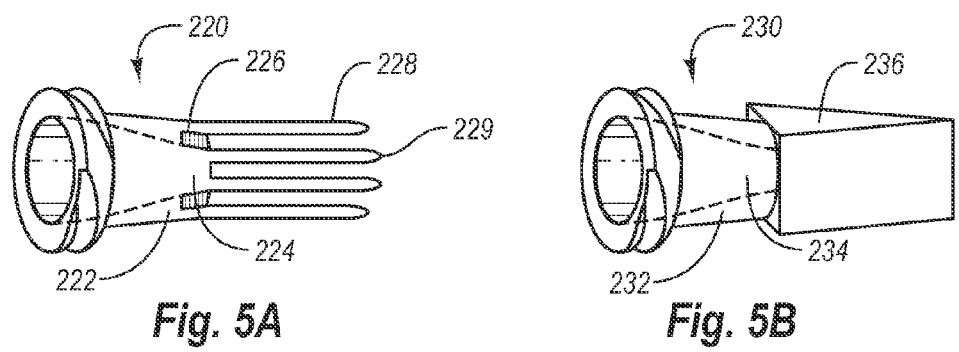
FIGS. 5A-5D are schematic representations of different embodiments of dental bleach applicators, each having a brush tip.

FIG. 5A is a schematic representation of an embodiment of a brush tip 220. As shown, the brush tip 220 has a tapered brush head 222 that defines a conduit 224 that extends therethrough. The brush head 222 and conduit 224 are coupled to a brush filament 228. The brush filament 228 is comprised of a plurality of fingers 229 that extend from the brush head 222, and a gap exists between each pair of fingers 229. Additionally, the brush filament 228 includes a plurality of activator reservoirs 226, which are disposed at the base of each gap. By having the activator reservoirs 226 being disposed at the base of each gap, the dental bleaching composition that is delivered through the conduit 224 comes into contact with the brush filament 228 so that the bleaching composition is activated by the activator before being dispensed. Also, the brush filaments 228 may include activators disposed therein that can further activate the dental bleaching composition while being applied to the teeth. Thus, the configuration of the brush tip applicator 220 enhances the efficiency of releasing the activator into the inactivated dental bleaching composition by providing reservoirs of the activator and/or providing an increased volume (e.g., fingers 229) of the filament for retaining the activator.

FIG. 5B is a schematic representation of an embodiment of a brush tip 230. As shown, the brush tip 230 has a tapered brush head 232 that defines a conduit 234 that extends therethrough. The brush head 232 and conduit 234 are coupled to a porous brush filament 236 that includes the dental bleach activator. The brush filament 236 is shown as a single, wedge-shaped filament 236; however, filaments of various shapes can be used. The porous brush filament 236 has a porosity that allows the bleaching composition to be delivered therethrough in a manner that provides for the activator to diffuse into the bleaching composition in order to activate the bleach. The wedge shape can be beneficial for painting the activated dental bleach onto the teeth, and can function similarly to wedge-shaped paintbrushes; however, other shapes, such as those used in other porous or polymeric paintbrush filaments, can be used as a porous brush filament 236. In an alternative to a porous filament, the filament can include an open cell configuration, closed cell configuration, memory foam, flexible foam, flexibly resilient foam, sponge, or the like.

Figures 5C, 5D:
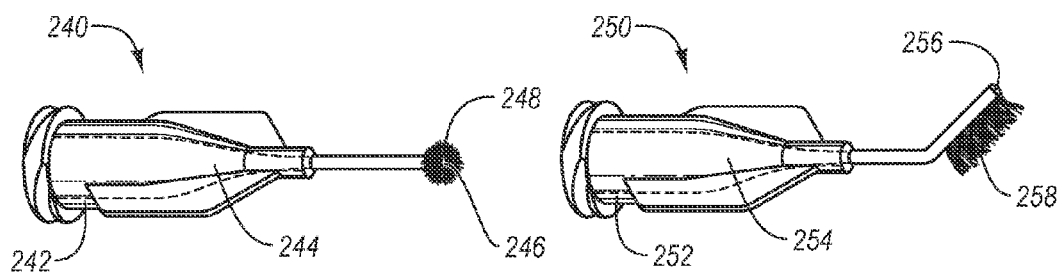

FIG. 5C is a schematic representation of an embodiment of a brush tip 240. As shown, the brush tip 240 has a tapered brush head 242 that defines a conduit 244 that extends therethrough. The conduit 244 is open at the distal end to form a conduit opening 246 for dispensing the dental bleaching composition. The brush head 242 and conduit 244 are coupled to a plurality of brush filaments 248 that are impregnated with the activator. Each brush filament 248 is configured as a bristle such that the combination of the plurality of brush filaments 248 have a large surface area that allows for increased contact with the dental bleaching composition so that the activator diffuses into and activates the dental bleaching composition. In use, the composition is applied to the teeth, and the plurality of brush filaments 248 is used to spread the composition so as to selectively apply the activated dental bleaching composition to the selected portion of the teeth.

FIG. 5D is a schematic representation of an embodiment of a brush tip 250. As shown, the brush tip 250 has a tapered brush head 252 that defines a conduit 254 that extends therethrough. The conduit 254 is open at the distal end to form a conduit opening 256 for dispensing the dental bleaching composition. The brush head 252 includes a plurality of brush filaments 258 that are impregnated with the activator and that are disposed adjacent to the conduit opening 256. Each brush filament 258 is configured as a bristle such that the combination of the plurality of brush filaments 258 have a large surface area that allows for increased contact with the dental bleaching composition so that the activator diffuses into and activates the dental bleaching composition. In use, the composition is applied to the teeth through the conduit opening 256, and brush head 252 is rotated so that the plurality of brush filaments 248 are then used to spread the composition and so as to selectively apply the activated dental bleaching composition to selected portion of the teeth.

The various embodiments of the present invention are not limited to those embodiments illustrated and described in connection with the figures. As such, various modifications to the dental bleach applicators and/or brush tips can be made by routinely combining, altering, or replacing various features. Additionally, any of the features of the illustrated and described embodiments of the dental bleach applicators and/or brush tips can be combined and/or exchanged from one embodiment to another embodiment. Also, various features can be omitted and still retain the basic functionality of the present invention. Alternatively, various features of dental bleach applicators and/or brush tip devices that are well known in the art, not depicted and described in connection with the figures, can be included with the present invention. For example, the activator reservoirs or depots can be used with any of the other embodiments, where such reservoirs or depots can be included within a brush filament or even in a brush head adjacent to a conduit. In another example, the applicator tube can be optional in cases where the brush tip can be directly attached to the portion of the applicator that retains the dental bleaching composition. In still another example, the conduit openings (e.g., holes for dispensing the dental bleaching composition from the brush tip) in the brush tip can include nozzles or extenders rather then merely being a hole in the brush head. In yet another example, the body of the applicator tip can be impregnated with the activator.

III. Compositions

The dental bleach applicator and brush tip of the present invention can be prepared from a variety of different materials. As such, any material that can be used for the functionalities of the dental bleach applicator, brush tip, and/or brush filament described herein can be applied to the present invention. Generally, the different features of the dental bleach applicator, brush tip, and/or brush filament can be prepared from different materials that impart the proper functionality. That is, such features are prepared from appropriate polymers, rubbers, ceramics, and metals. Also, the individual features of the dental bleach applicator, brush tip, and/or brush filament described herein that are known in the art can be prepared from standard materials. For example, the applicator syringe is prepared of plastics, the brush tip is metal, and the brush filament is a fibrous, polymeric, and/or flocked material.

The materials utilized in the applicator body and tip can be comprised of most materials. However, it is preferable for the material to be a metal or polymer. Metals are advantageous because a number of different types of alloys are prepared to have different properties, such as chemical resistance. Also, metals are prepared into almost any shape. Polymers are advantageous because they are formulated into a number of plastics and elastomers that can be adapted for use in a syringe or other type of applicator. Also, polymers can be configured to be resistant to the inactive or substantially inactive bleaching composition that is retained within the body of the applicator. Polyolefins, such as polyethylenes, and glasses are commonly used for syringes.

In one embodiment, the brush filament can be substantially similar to a bristle of a toothbrush, paint brush, hair brush, cleaning brush, or the like. For example, the brush filament has physical and/or chemical properties similar to the bristle of a toothbrush; however, the shape and size of the filament can be varied, and are usually smaller than the bristles of a toothbrush. For example, the filament is prepared from a polymeric material that forms a matrix for retaining the activator during storage and allows the activator to be released therefrom during use. Examples of materials commonly used for bristles of toothbrushes that are prepared into a brush filament include nylons, polyamides, polyesters, polyolefins, polypropylenes, polyvinylpyrrolidone, and the like. Additionally, the filament can be comprised of natural fibers (e.g., cotton), celluloses, gums, carbopolymers, any water-dispersible polymers, and the like. The filament is in a dry state prior to use so as to be substantially devoid of being gummy, sticky, or the like.

In one embodiment, the brush tip is a flocked tip. That is, the brush tip is flocked so as to have a plurality of filaments. Each of the flocked fibers are flocked or otherwise attached to the periphery surface of the tip. The flocked tip includes at least one type of flocked fiber; however, multiple types of flocked fibers can be used. The flocked fibers may be composed of various natural materials (e.g., cotton), polymers, metals, ceramics, or any combination thereof. Suitable polymers include polyolefins, polypropylenes, polyethylenes, polyamides, nylons, polyvinylpyrrolidones, polyesters, and the like. Suitable metals include tungsten, titanium, titanium alloys, stainless steel, other types of steel, copper, copper alloys (e.g., brass and bronze), aluminum alloys, nickel, nickel alloys, and the like. Suitable ceramics include carbon (e.g., graphite) and boron fibers. It is preferred that at least one of the flocked fibers is a polymer impregnated with the dental bleach activator.

In one embodiment, the filaments have a uniform length or varying lengths. A preferred length is within the range from about 0.1 mm to about 5 mm, and more preferably within a range from about 0.5 mm to about 3 mm, and most preferably within a range from about 0.7 mm to about 1.5 mm. The diameters of the filaments may also vary, preferably within a range from about 1 Denier to about 20 Denier, more preferably within a range from about 1.5 Denier to about 15 Denier, and most preferably within a range from about 3 Denier to about 10 Denier. It will be appreciated that the length and diameter of the filaments, as well as the texture, flexibility, and the density of distribution of the filaments may vary to accommodate different needs and preferences. Additionally, single filament embodiments are substantially larger, and have dimensions that are compatible as described herein with respect to the contact area.

The filaments are attached to the tip surface by any suitable process, such as a fastener, adhesive, flocking, electrostatic flocking, injection molding, welding, combinations thereof, and the like. In one embodiment, the filaments are electrostatically flocked onto the flocked tip and secured by an adhesive. Optionally, the adhesive is a flexible and water insoluble adhesive, such as a polyurethane or flexible acrylic adhesive. Flexible adhesives are particularly useful when the fibers are stiff or rigid because it allows the fibers to bend at their points of affixation. It should be appreciated, however, that other adhesives such as epoxies, polyisobutylenes, and silicones can also be used. Optionally, the activator is imbedded in the adhesive.

The activator is imbedded within the filament by a variety of processes that allows for the filament to control the release of the activator. Any process that includes the activator within a polymer may be used to imbed the activator within the filament. For example, the filament and activator are mixed together, extruded together, cast together, or other process where a material that is formed into the filament is prepared to include the activator. Alternatively, the filament is absorbed into the filament by placing the filament into a proper solution containing the activator. In another alternative embodiment, a composition comprising the activator is coated onto the filament and/or onto any portion of the applicator tip. In another alternative, a polymeric coating is applied to the filament so as to provide for controlled release of the activator from the filament.

In one embodiment, the applicator tip is comprised of a metal body having flocked nylon adhered thereto. The flocked nylon is attached to the metal body by any suitable adhesive that is compatible with nylon. While substantially any metal can be used, stainless steels are preferred.

The dental bleaching composition is any dental composition that is capable of whitening teeth. This includes a composition having a therapeutically effective amount of a bleaching compound that can be activated by an activator (e.g., catalytic agent) and whiten the teeth of a subject. The amount of activator is a therapeutically effective amount that is capable of inducing the reaction of a significant portion of the bleaching compound within a short period of time. A bleaching compound is characterized as any compound which has the ability, when activated by an activator, of whitening the teeth. Examples of suitable bleaching compounds include any oxygen radical generating agent, such as metal ion free peroxides, organic peroxides, metal ion containing peroxides, and the like. Specific examples of bleaching agents suitable for use with an activator are carbamide peroxide, carbamyl peroxide, sodium percarbonate, perhydrol urea, and hydrogen peroxide. Additionally, other bleaching agents that are typically included in two-part bleaching systems can be included in the dental bleaching composition of the present invention.

In one embodiment, the bleaching agent employed in the dental bleaching composition is present in amounts so that about 3% to 40% by weight comprises the bleaching agent or effective amount of hydrogen peroxide. Preferably, the bleaching compound is present in an amount such that the effective concentration of the bleaching compound is from about 3% to about 38% by weight, more preferably from about 10% to about 35%, and most preferably from about 20% to about 30% by weight. However, it is recognized that different bleaching agents can be present at different concentrations in order to obtain the effective concentration.

In one embodiment, the bleaching agent is contained in an acceptable carrier. Carrier formulations for bleaching agents are well known in the art. The carrier formulation may be aqueous or non-aqueous. As an example, glycerin, and polyethylene glycol in combination with water can be used in formulating the carrier. Thickening or gelling agents may also be used in the carrier formulation of the bleaching agent. In one example, poloxyethylene/polyoxypropylene block copolymers can be utilized. As another example, carbopol polymers can be used. Additionally, other well-known components of bleaching agent compositions can be used in the bleaching compositions of the present invention.

The activator is any agent that activates the bleaching agent into an active form or a more active form that whitens teeth. In one embodiment, the activator is a catalytic agent, which is a compound or molecule that accelerates the whitening action of the bleaching compound without being consumed in the reaction. In another embodiment, the activator is a compound or molecule that is consumed in the reaction that activates the bleaching compound. The activator accelerates the release of oxygen radicals from an oxygen radical generating agent. Examples of activators include substances comprised of activated charcoal, platinum, platinum salts, copper, copper salts, palladium, palladium salts, silver, silver salts, $MnO_2$, FeO, $Fe_2O_3$, ferric sulfate, ferric subsulfate, potassium salts, iodide salts, potassium iodide, sodium iodide, iodine, enzyme (e.g., catalase or other suitable enzyme) and the like. The activator can be water soluble or insoluble. Additionally, other activators that can activate bleaching agents that are typically included in two-part bleaching systems can be included in the dental bleaching composition of the present invention. Also, thiosulfate can be used to help in disassociating ions of an activator, such as separating iodine into $I^-$ ions, or preventing the association of two ions.

In one embodiment, the bleaching agent activators include bases (i.e., substances that raise the pH in aqueous systems). Examples of useful bases that activate bleaching agents, and thereby accelerate bleaching include oxides, hydroxides, carbonates, and bicarbonates of alkali metals and alkaline earth metals, and amines. Examples include sodium oxide, sodium hydroxide, potassium oxide, potassium hydroxide, sodium carbonate, sodium bicarbonate, ammonium hydroxide, magnesium hydroxide, sodium phosphate tribasic, and ethanolamine. Bases, when used as bleaching agent activators, are preferably included in the filament at an amount in a range of about 0.1% to about 20% by weight, more preferably in a range of about 1% to about 10% by weight, and most preferably about 7% by weight.

In one embodiment, the bleaching agent activators include metals and metal compounds. Examples of metals and metal compounds include transition metals (e.g., powders or fine particulates of iron, cobalt, nickel, copper, zinc, manganese, chromium, and the like), metal compounds (e.g., halides or sulfates of iron, cobalt, nickel, copper, zinc, manganese, chromium, and the like), and salts thereof. More specific examples include iron and manganese metal, manganese chloride, manganese citrate, ferrous sulfate, and manganese sulfate.

In one embodiment, the bleaching agent activators include enzymes, particularly organo-metallic enzymes containing transition metals, such as iron. One example is "catalase", which is described more particularly in U.S. Pat. No. 6,485,709 and incorporated herein by specific reference.

Metals, metal compounds, salts, and enzymes, when used as a bleaching agent activator, are preferably included in the filament in an amount ranging from about 0.01% to about 20% by weight, more preferably in a range of about 0.05% to about 10% by weight, and most preferably in a range of about 0.1% to about 5% by weight.

The activators activate a significant portion of the bleaching compound within a short period of time of coming into contact with the bleaching compound. This includes activation in less than about 30 minutes, more preferably less than about 20 minutes, and most preferably in about 10 minutes or less.

In one embodiment, the amount of activator disposed in the applicator tip is sufficient to activate substantially all of the bleaching compound. However, the activator may activate a cumulative amount per session, cumulative amount per application, or one-time dispensed amount of about 25% of the bleaching agent, preferably about 50% of the bleaching agent, more preferably about 70% of the bleaching agent, and most preferably about 90% of the bleaching agent.

In one embodiment, the amount of activator disposed in the applicator tip (e.g., body, filament, adhesive, and the like) is sufficient to activate the beaching compound for multiple bleaching sessions. That is, the same applicator tip is used in multiple bleaching sessions with the same applicator body or with multiple applicator bodies. As such, the amount of activator disposed in the applicator tip is sufficient for at least 2 bleaching applications, more preferably for at least 3 bleaching applications, even more preferably for at least 4 bleaching applications, and most preferably for at least 5 bleaching applications. Typically, a session can include 1-4 bleaching applications, and each application can be about 15-20 minutes of bleaching.

In one embodiment, a stable activator composition is formed that includes the activator microencapsulated into a polymeric particle. Techniques for microencapsulation of individual components for tooth and gum dentifrice are well known in the art (see U.S. Pat. No. 5,403,578, which is incorporated herein by specific reference). The encapsulated activator is stable until contacted with the dental bleaching composition and/or saliva, which contains water.

In one embodiment, the activator is to be used to enhance the bleaching activity of the bleaching composition. As such, a variety of standard bleaching agents can be utilized in the bleaching composition, such as bleaching agents commonly found in single bleaching composition protocols. Examples of suitable bleaching agents include aqueous hydrogen peroxide, carbamide peroxide, benzoyl peroxide, glyceryl peroxide, percarbonates and perborates of alkali and alkaline earth metals (e.g., sodium perborate) and peroxyacetic acid. The bleaching agents are preferably included in a range from about 0.5% to about 50% by weight of the dental whitening composition, more preferably in a range from about 1% to about 30% by weight and most preferably in a range from about 3% to about 20% by weight. These concentrations can also represent the effective hydrogen peroxide concentrate.

In one embodiment, the dental bleaching composition includes an ion scavenger. In order to preserve the stability of the dental bleaching compositions, an ion scavenger such as EDTA, salts of EDTA, or others is included. Additionally, ion scavengers such as citric acid, succinic acid, adipic acid, nitrates and phosphates of tin and any other commonly used chelating agents may be used. Ion scavengers are preferably included in an amount in a range from about 0% to about 1% by weight of the dental whitening composition, more preferably in a range from about 0.03% to about 0.5% by weight and most preferably in a range from about 0.05% to about 0.2% by weight.

In one embodiment, potassium nitrate is included in the dental bleaching composition. A significant advantage of using potassium nitrate in combination with a bleaching agent in a tooth whitening composition is that the potassium nitrate simultaneously decreases the sensitivity of the teeth that may result from the use of the bleaching agent. Accordingly, potassium nitrate provides for desensitization. Other desensitizing agents can also be used to desensitize teeth, including citric acid, citric acid salts, strontium chloride, and the like. Fluoride salts, when used in combination with a peroxide dental bleaching agent, have also been found to inherently offset tooth sensitivity that may be caused by the peroxide bleaching agent. The potassium nitrate is preferably included in an amount of about 0.01% to about 2% by weight of the dental composition, and more preferably in an amount of about 0.05% to about 1% by weight.

In one embodiment, an antimicrobial agent is included in the bleaching composition. Examples of useful antimicrobial agents include chlorohexidine, tetracycline, cetyl pyridinium chloride, benzalkonium chloride, cetyl pyridinium bromide, methyl benzoate, and propyl benzoate. The antimicrobial agents are preferably included in an amount in a range from about 0% to about 15% with the dental whitening composition, more preferably in a range from about 1% to about 5% by weight.

In one embodiment, an abrasive material is used with the bleaching composition of the invention. For example a dicalcium phosphate abrasive may be incorporated into the composition (see U.S. Pat. No. 5,171,564, which is incorporated here by specific reference). Example of dicalcium phosphate abrasives include, but are not limited to dicalcium phosphate dihydrate, anhydrous dicalcium, or calcium pyrophosphate. Other abrasives can be used with the subject invention, such as silica abrasives, such as precipitated amorphous hydrated silica, and alumina abrasives, such as alumina trihydrate, aluminum silicate, calcined alumina, and bentonite.

In one embodiment, it is beneficial for the bleaching composition to include water, a humectant, a surfactant, and/or a thickener. Examples of humectants are glycerin, sorbitol, and polyethylene glycol (molecular weight 200-1000). Both mixtures of humectants and single humectants can be employed in the composition of the invention. Thickeners may be incorporated in the abrasive component such as natural and synthetic gums such as carrageenans, xantham gums, talha gums, tragacanth gums, locust bean gum, guar gum, ghatti gum, furcellaran gum, arabic gum, alginic acid gum, agar gum, alginate gum, carboxypolymethylenes, carboxymethyl celluloses, starches, polyvinylpyrrolidones, hydroxyethylpropyl- celluloses, hydroxybutyl methyl celluloses, hydroxypropyl methyl celluloses, hydroxyethyl celluloses, and the like.

In one embodiment, a polyol is used as a solvent for the dental bleaching composition. The solvent may also be water alone or in combination with a polyol. Glycerin is a preferred solvent as it works well in forming a sticky gel with carboxy- polymethylene. Glycerin also provides some flavor enhancement. A few possible substitutes for glycerin include propylene glycols, polypropylene glycol, polyethylene glycols, eryrthritol, sorbitol, mannitol, other polyols, and the like.

Since highly acidic compositions can etch teeth, it is generally preferable to adjust the pH of dental compositions that include acids to be less acidic. Accordingly, it is preferable to adjust the pH of the bleaching compositions to within a range from about 4 to about 9, more preferably to within a range from about 5 to about 8, and most preferable within a range from about 6.5 to about 7.5. Preferred bases used to adjust the pH of the dental compositions may include inorganic bases such as sodium hydroxide or ammonium hydroxide. Alternatively, the base may include an organic base such as triethanolamine or other organic amines.

In one embodiment, an agent for administering fluoride, such as a fluorine providing salt, may be incorporated into the bleaching composition. Such materials are characterized by their ability to release fluoride ions in water. Agents for administering fluoride include, but are not limited to, inorganic metal salts such as sodium fluoride, potassium fluoride, and tin fluoride such as stannous fluoride or stannous chlorofluoride, sodium fluorosilicate, ammonium fluorosilicate, and sodium monofluorophosphate.

In one embodiment, the bleaching composition may also include palliative ingredients for periodontal tissues. Examples of such ingredients include, but are not limited to aloe, eugenol, and vitamin E. Pigments, sweeteners, colors, and flavors may also be incorporated into the composition.

Additionally, any approved dye may be used in the bleaching composition of the present invention. Aesthetic water soluble dyes are preferred. The use of a dye prevents an accidental application of the bleaching composition to the gingiva since it can be easily seen and provides the user with a control mechanism to time the duration of the bleaching operation and bleaching action. Additionally, dyes that absorb light energy can be used. Such light-absorbing dyes can help activate the dental bleaching composition when an appropriate light is directed onto the bleaching composition. Beta-carotene can also be used.

IV. Methods of Whitening Teeth

As generally described above, the present invention provides a method for whitening teeth. Such a method is implemented by utilizing the dental bleach applicator and/or applicator tip as described herein. Accordingly, the method is performed by providing a bleaching agent that is activated or further activated, providing a brush filament containing an activator that activates or further activates the bleaching agent, and then combining the bleaching agent with the brush filament such that the activator activates a significant portion of the bleaching agent so as to be capable of whitening teeth. At some point in the process, the bleaching agent is coated onto at least a portion of the teeth with the applicator tip. The applicator tip is dimensioned such that a minimal amount of the activated bleaching agent comes into contact with the gums, buccal tissue, lips, or tongue so as to inhibit chemical burns caused by the activated bleaching agent.

The bleaching agent is mixed with the activator by contacting the bleaching agent with the brush filament for a time sufficient for the activator to intermingle with the bleaching agent prior to or during use of the bleaching agent. For example, the bleaching agent can be in a liquid, gel, paste, or other similar form, and the activator is retained within the polymeric matrix of the brush filament. Just prior to or during use, the dental bleaching composition containing the bleaching agent is contacted with the brush filament so as to activate the bleaching agent.

In one embodiment, a single container is compartmentalized so the bleaching agent is housed therein and separately from the brush filament containing the activator. Upon being dispensed from the container, the bleaching agent is combined with the brush filament having the activator. For example, the bleaching agent and activator are admixed on the brush filament. The brush filament is then used for brushing the bleaching agent and activator onto the teeth for a sufficient time to allow for the bleaching agent to be activated.

In one embodiment, the dental bleaching composition is dispensed onto a substrate from the brush tip, and the brush tip having the brush filaments containing the activator is then used to mix the activator into the dental bleaching composition. The activated dental bleaching composition is then applied to the teeth as described herein with the brush tip having the brush filament.

In one embodiment, the bleaching agent is not applied to the surface of a toothbrush and/or the activator is not included within a toothbrush bristle. A toothbrush is a device designed for cleaning teeth that has a region for holding, such as a handle, and a region for cleaning, such as bristles or a sponge, and have contact surface areas larger than the surface of a tooth. Since a toothbrush is either manually or mechanically agitated to clean the teeth of a subject, the large brush head allows the bristles to contact the gums, buccal tissue, lips, and/or tongue. Such contact with the activated bleaching agent can cause chemical burns, which is not favorable. Thus, it is beneficial to avoid the use of an applicator tip configured as a toothbrush having such a large head with the present invention.

It should be noted that any number or configuration of brush filaments can be embedded with the activator. The bleaching agent is applied to the brush filament prior to use of the applicator. The application of the activated bleaching agent with the brush tip applicator results in the activator activating the bleaching agent. The activated bleaching agent is then applied to the teeth, and the whitening effect is thereby achieved.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Additionally, all references recited herein are incorporated in their entirety by specific reference.

What is claimed is:

1. A brush tip for applying a dental bleaching composition to teeth, the brush tip comprising:
   an applicator tip having a body defining an external surface and an internal conduit fluidly coupled to a conduit opening, said body having a proximal end defining a proximal opening of the internal conduit, said proximal end having a first fastener for being coupled to a second fastener of a member containing a dental bleaching composition, said body having a distal end defining a distal opening of the internal conduit through which a dental bleaching composition exits during use of the brush tip;
   at least one filament disposed on the external surface and at the distal end of the body and forming a contact area when in contact with a tooth that is less than a surface area of the tooth; and
   a dental bleach activator disposed on or within the filament in an amount sufficient for activating a dental bleaching composition for whitening teeth,
   the brush tip providing that the dental bleach activator does not contact a dental bleaching composition before exiting the distal opening of the internal conduit.

2. A brush tip as in claim 1, wherein the at least one filament includes an amount of activator sufficient for multiple applications of the dental bleaching composition to teeth.

3. A brush tip as in claim 2, wherein the amount of activator is sufficient for activating an amount of the dental bleaching composition sufficient for at least two separate applications of the dental bleaching composition to the teeth.

4. A brush tip as in claim 1, wherein the filament is comprised of a polymer impregnated with dental bleach activator.

5. A brush tip as in claim 4, wherein the polymer is configured so as to control the release of the dental bleach activator into the dental bleaching composition.

6. A brush tip as in claim 5, wherein the polymer is comprised of polyvinylpyrrolidone or nylon.

7. A brush tip as in claim 1, wherein the filament is at least one of a bristle, flocked member, porous body, or foam.

8. A brush tip as in claim 1, wherein the conduit opening is disposed on a distal end of the tip body.

9. A brush tipped applicator for initially storing and then applying a dental bleaching composition to teeth, the applicator comprising:
   an applicator body having a reservoir that contains therein a dental bleaching composition and a dispenser mechanism configured for dispensing the dental bleaching composition onto teeth; and
   a brush tip coupled to the applicator body, the brush tip comprising:
      an applicator tip having a body defining an external surface and an internal conduit fluidly coupled to a conduit opening, said body having a proximal end defining a proximal opening of the internal conduit, said proximal end being coupled to the applicator body such that the internal conduit of the body is capable of being fluidly coupled with the dental bleaching composition, said body having a distal end defining a distal opening of the internal conduit through which the dental bleaching composition exits during use of the brush tip;
      at least one filament disposed on the external surface and at the distal end of the applicator tip body; and
      a dental bleach activator disposed on or within the filament in an amount sufficient for activating the dental bleaching composition for whitening the teeth,
      the brush tip providing that the dental bleach activator does not contact the dental bleaching composition before exiting the distal opening of the internal conduit.

10. A brush tipped applicator as in claim 9, wherein the at least one filament includes an amount of activator sufficient for multiple applications of the dental bleaching composition to teeth.

11. A brush tipped applicator as in claim 10, wherein the amount of activator is sufficient for activating an amount of the dental bleaching composition sufficient for at least two separate applications of the dental bleaching composition to the teeth.

12. A brush tipped applicator as in claim 9, wherein the filament is comprised of a polymer impregnated with dental bleach activator.

13. A brush tipped applicator as in claim 12, wherein the polymer is configured so as to control the release of the dental bleach activator into the dental bleaching composition.

14. A brush tipped applicator as in claim 13, wherein the polymer is comprised of polyvinylpyrrolidone or nylon.

15. A brush tipped applicator as in claim 9, wherein the filament is at least one of a bristle, flocked member, porous body, or foam.

16. A brush tipped applicator as in claim 9, wherein the at least one filament forms a contact area when in contact with a tooth, said contact area being less than the surface area of a front surface of a tooth.

17. A brush tipped applicator as in claim 9, wherein the at least one filament forms a contact area when in contact with a tooth, said contact area being less than about 1 $cm^2$.

18. A brush tipped applicator as in claim 9, said proximal end of the applicator tip having a first fastener removably coupled to a second fastener of the applicator body.

19. A brush tipped applicator as in claim 9, wherein the applicator body is a syringe.

20. A brush tipped applicator as in claim 9, wherein the applicator body is not a tooth brush.

* * * * *

UNITED STATES PATENT AND TRADEMARK OFFICE
CERTIFICATE OF CORRECTION

PATENT NO.        : 7,740,479 B2
APPLICATION NO.   : 11/866532
DATED             : June 22, 2010
INVENTOR(S)       : Allred et al.

It is certified that error appears in the above-identified patent and that said Letters Patent is hereby corrected as shown below:

Column 1
Line 62, change "of prior art" to --of the prior art--

Column 2
Line 41, change "being," to --being--

Column 3
Line 11, change "2" to --two--

Column 4
Line 18, remove [in] after "within"

Column 5
Lines 60-62, change all instances of "ul" to --µl--

Column 8
Line 59, change "applicator 112" to --applicator brush 112--

Column 9
Line 13, change "Figure A" to --Figure 4A--

Column 10
Line 28, change "brush filaments 248" to --brush filaments 258--

Column 11
Line 43, change "fiber;" to --fiber,--

Column 13
Line 10, change "poloxyethylene/polyoxypropylene" to --polyoxyethylene/polyoxypropylene--

Signed and Sealed this

Twenty-third Day of November, 2010

David J. Kappos
*Director of the United States Patent and Trademark Office*

Column 14
Line 17, change "beaching" to --bleaching--

Column 18
Line 35, change "to teeth" to --to the teeth--